United States Patent
Jang et al.

(10) Patent No.: US 11,248,201 B2
(45) Date of Patent: Feb. 15, 2022

(54) CELL CULTURE VESSEL

(71) Applicant: AMOLIFESCIENCE CO., LTD., Seoul (KR)

(72) Inventors: Seon Ho Jang, Seoul (KR); Song Hee Koo, Gimpo-si (KR); In Yong Seo, Seoul (KR); Seoung Hoon Lee, Paju-si (KR); Chan Kim, Gwangju (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 86 days.

(21) Appl. No.: 16/630,019

(22) PCT Filed: Jul. 13, 2018

(86) PCT No.: PCT/KR2018/007945
§ 371 (c)(1),
(2) Date: Jan. 10, 2020

(87) PCT Pub. No.: WO2019/013580
PCT Pub. Date: Jan. 17, 2019

(65) Prior Publication Data
US 2021/0087509 A1 Mar. 25, 2021

(30) Foreign Application Priority Data
Jul. 13, 2017 (KR) .................. 10-2017-0089071

(51) Int. Cl.
*C12M 3/00* (2006.01)
*C12M 1/12* (2006.01)
*C12M 1/32* (2006.01)

(52) U.S. Cl.
CPC ............ *C12M 23/46* (2013.01); *C12M 23/12* (2013.01); *C12M 25/02* (2013.01); *C12M 25/04* (2013.01); *C12M 25/14* (2013.01)

(58) Field of Classification Search
CPC ...... C12M 23/46; C12M 23/12; C12M 25/04; C12M 25/14; C12M 25/02; C12M 23/34; C12M 21/08
(Continued)

(56) References Cited

U.S. PATENT DOCUMENTS 8,470,597 B2 * 6/2013 Chiou ................. A61L 27/3834
435/325
2010/0255581 A1 10/2010 Naqvi et al.
(Continued)

FOREIGN PATENT DOCUMENTS

EP 2 348 097 A1 7/2011
JP 2010-098979 A 5/2010
(Continued)

OTHER PUBLICATIONS

Extended Search Report cited in EP 18832793.6 dated Apr. 26, 2021, 8 pages.

*Primary Examiner* — Michael L Hobbs
*Assistant Examiner* — Lenora A Abel
(74) *Attorney, Agent, or Firm* — Rothwell, Figg, Ernst & Manbeck, P.C.

(57) ABSTRACT

A cell culture vessel including an accommodating part which is an inner space accommodating a cell culture support therein, a fixing member configured to fix the cell culture support to a lower surface of the accommodating part, wherein the fixing member includes a first adhesive layer attached to the lower surface of the accommodating part, a second adhesive layer attached to a lower surface of the cell culture support, and a support film interposed between the first adhesive layer and the second adhesive layer and configured to perform a support function, and an adhesive force between the second adhesive layer and the cell culture support is higher than an adhesive force between
(Continued)

the first adhesive layer and the lower surface of the accommodating part.

7 Claims, 3 Drawing Sheets

Specification includes a Sequence Listing.

(58) Field of Classification Search
USPC .................................................. 435/289.1
See application file for complete search history.

(56) References Cited

U.S. PATENT DOCUMENTS

| | | | |
|---|---|---|---|
| 2011/0207220 A1* | 8/2011 | Okano | C12N 11/02 |
| | | | 435/402 |
| 2013/0071918 A1* | 3/2013 | Kim | C12M 23/10 |
| | | | 435/305.1 |

FOREIGN PATENT DOCUMENTS

| | | |
|---|---|---|
| JP | 2013-099286 A | 5/2013 |
| JP | 2016-013111 A | 1/2016 |
| KR | 10-2008-0109086 A | 12/2008 |
| KR | 10-2011-0135211 A | 12/2011 |
| KR | 10-2014-0048733 A | 4/2014 |
| KR | 10-2014-0080899 A | 7/2014 |
| WO | 2014112633 A1 | 7/2014 |
| WO | 2016-068266 A | 5/2016 |

* cited by examiner

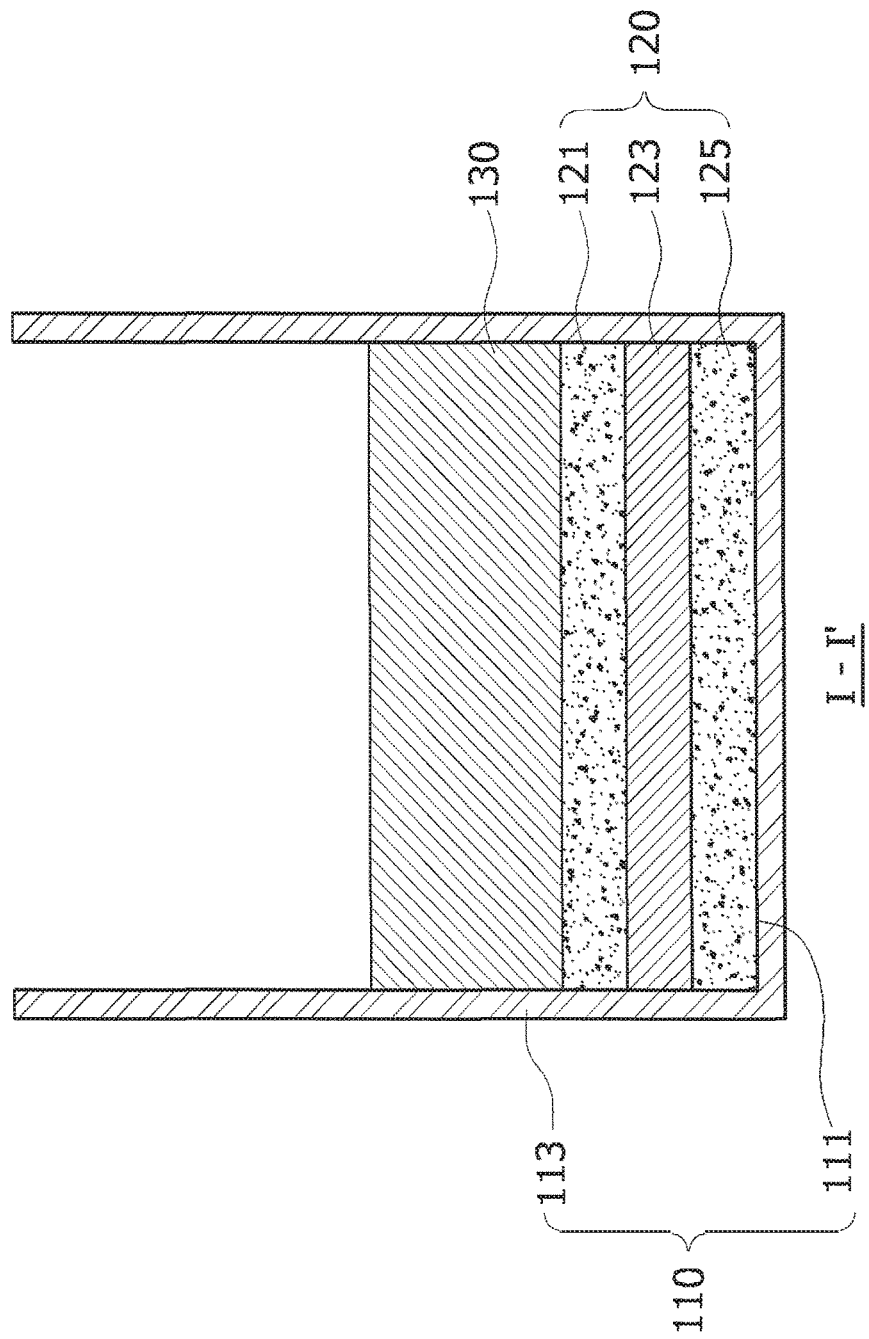

CELL CULTURE VESSEL

CROSS REFERENCE TO RELATED APPLICATION

This application is a 35 U.S.C. 371 National Phase Entry Application from PCT/KR2018/007945, filed Jul. 13, 2018, which claims the benefit of Korean Patent Application No. 10-2017-0089071 filed on Jul. 13, 2017, the disclosure of which is incorporated herein in its entirety by reference.

The instant application contains a Sequence Listing which has been submitted via EFS-Web and is hereby incorporated by reference in its entirety. Said Sequence Listing, created on Jan. 9, 2020, is named SOP115253US_Sequence Listing.ST25.txt and is 11 kilobytes in size.

TECHNICAL FIELD

The present invention relates to a cell culture vessel, and more particularly, to a cell culture vessel capable of providing a uniform microenvironment to each cultured cell while allowing the cultured cells to be easily recovered without causing damage to the cultured cells.

BACKGROUND ART

In recent years, with expansion of the use of cultured cells for the treatment of diseases, interest and research on cell culture have been increased. Cell culture is a technology for harvesting cells from living organisms and culturing the cells in vitro. Cultured cells may be differentiated into various tissues of the human body such as skin, organs, nerves, and the like and then transplanted into the human body or may be transplanted into the human body in a state before differentiation so as to be utilized in treating a variety of diseases by allowing engraftment and differentiation to occur simultaneously.

Tissue engineering is a field related to cell culture and is a multidisciplinary study that applies existing scientific fields such as cytology, life sciences, engineering, and medical science. Research on a new fusion technology has been carried out to understand the correlation between structure and function of biological tissues and to replace and regenerate damaged tissues or organs with normal tissues.

Meanwhile, in the field of regenerative medicine, research has been carried out to improve medical effects by manufacturing a cell culture support and a cell culture vessel so that cells harvested from a patient can be cultured in vitro and transplanting the cells cultured in the cell culture support back into the living body.

However, regarding cell culture supports and cell culture vessels which have been developed so far, because the cell culture support is firmly attached to the cell culture vessel, it is not easy to detach the cell culture support from the cell culture vessel without causing damage to the cell-cell binding of the cell culture support. Also, when, in order to solve this, the cell culture support is loosely fixed to the cell culture vessel, there is a problem of uniformity reduction due to a difference in physical and chemical stimulations on each cell because it is not possible to provide a uniform environment to each cultured cell.

In addition, because, in general, cells are very sensitive to biochemical and other external influences, applying a chemical mechanism to detach the cell culture support from the cell culture vessel is not appropriate as a method for obtaining uniformly cultured cells.

Further, in the case of colony cells constituting a colony, even when cell colonies proliferated, not only the shape of the cell culture support in which the cells proliferated, but also the shapes of the cell colonies may be different according to physical and chemical methods of detaching from the cell culture support. When the shapes of the cell colonies are not uniform, each cultured cell colony may show a different reaction, and in this case, there is a problem in that, because it is not possible to derive reproducible results, the proliferated cell colonies are very unsuitable for use in testing and experimenting.

Accordingly, there is an urgent need to develop a technology capable of providing the same microenvironment to each cell in the process of culturing cells while allowing a cell culture support to be easily separated from a cell culture vessel without causing damage to cells cultured in the cell culture support.

DISCLOSURE

Technical Problem

The present invention is directed to providing a cell culture vessel capable of preventing shaking of a support and applying the same mechanical, physical, and chemical stimulations to each cultured cell, thereby allowing the cells to uniformly proliferate.

The present invention is also directed to providing a cell culture vessel capable of allowing a cell culture support, in which cells are cultured, to be easily recovered from the cell culture vessel.

The present invention is also directed to providing a cell culture vessel capable of culturing cells having a shape suitable for desired tests and experiments without causing damage to the cells in the process of separating a cell culture support.

The present invention is also directed to providing a cell culture support, in which cell colonies are cultured in a uniform shape and the cell-cell binding is not broken, and a cell culture vessel including the same.

Technical Solution

One aspect of the present invention provides a cell culture vessel including an accommodating part which is an inner space accommodating a cell culture support therein, the cell culture vessel including a fixing member configured to fix the cell culture support to a lower surface of the accommodating part, wherein the fixing member includes a first adhesive layer attached to the lower surface of the accommodating part, a second adhesive layer attached to a lower surface of the cell culture support, and a support film interposed between the first adhesive layer and the second adhesive layer and configured to perform a support function, and an adhesive force between the second adhesive layer and the cell culture support is higher than an adhesive force between the first adhesive layer and the lower surface of the accommodating part.

According to an embodiment of the present invention, an adhesive force ratio of the adhesive force between the first adhesive layer and the lower surface of the accommodating part to the adhesive force between the second adhesive layer and the cell culture support may be 1:1.3 to 1:4.

Also, an adhesive force ratio of the adhesive force between the first adhesive layer and the lower surface of the accommodating part to the adhesive force between the second adhesive layer and the cell culture support may be 1:1.5 to 1:3.

Also, the adhesive force between the first adhesive layer and the lower surface of the accommodating part may be in a range of 3 to 30 gf/inch.

Also, the adhesive force between the second adhesive layer and the cell culture support may be in a range of 7 to 60 gf/inch.

Also, the first adhesive layer and the second adhesive layer may each independently include one or more selected from the group consisting of a silicone-based adhesive and a urethane-based adhesive.

Also, the first adhesive layer may have a thickness in a range of 7 to 55 μm.

Also, the second adhesive layer may have a thickness in a range of 3 to 25 μm.

Also, the support film may have a thickness in a range of 30 to 220 μm.

Also, the support film may include one or more selected from the group consisting of polyethylene, polypropylene, polyimide, cross-linked polypropylene, nylon, polyurethane-based resin, acetate, polybenzimidazole, polyimideamide, polyetherimide, polyphenylene sulfide (PPS), polyethylene terephthalate (PET), polytrimethylene terephthalate (PTT), polybutylene terephthalate (PBT), polyvinylidene fluoride (PVDF), polytetrafluoroethylene (PTFE), polychlorotrifluoroethylene (PCTFE), and polyethylene tetrafluoroethylene (ETFE).

Also, the cell culture support may be a fabric including any one or more of a knit, a woven fabric, and a nonwoven fabric.

Also, the fabric may include a cell culture enhancing substance.

Also, the cell culture enhancing substance may include a bioactive component that induces any one or more of adhesion, migration, growth, proliferation, and differentiation of cells.

Amino acid sequences used in the present invention are abbreviated as shown in Table 1 below according to the IUPAC-IUB nomenclature.

TABLE 1

| IUPAC-IUB nomenclature | Symbol | Abbreviation |
| --- | --- | --- |
| Alanine | A | Ala |
| Arginine | R | Arg |
| Asparagine | N | Asn |
| Cysteine | C | Cys |
| Glutamic acid | E | Glu |
| Glutamine | Q | Gln |
| Glycine | G | Gly |
| Histidine | H | His |
| Isoleucine | I | Ilt |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Advantageous Effects

According to the present invention, because non-uniform dispersion of a culture solution due to shaking of a support and tipping of the culture solution due to migration of cells being cultured can be prevented in the process of culturing the cells, it is possible to contribute to uniform cell proliferation by applying the same mechanical, physical, and chemical stimulations to each cell.

Also, because a cell culture support can be easily separated from a cell culture vessel, it is possible to prevent degeneration or desorption of cells due to biochemical mechanisms and to prevent damage to cultured cells due to stimulation more than necessary to the cultured cells.

Further, in the case of colony cells that proliferate and form colonies, it is possible to prevent degradation of uniformity in the shapes of the colonies due to a difference in physical and chemical stimulations applied to each colony in the process of recovering a cell culture support.

DESCRIPTION OF DRAWINGS

FIG. 3 is a cross-sectional view taken along line I-I' illustrated in FIG. 1.

BEST MODE OF THE INVENTION

Figure 1:
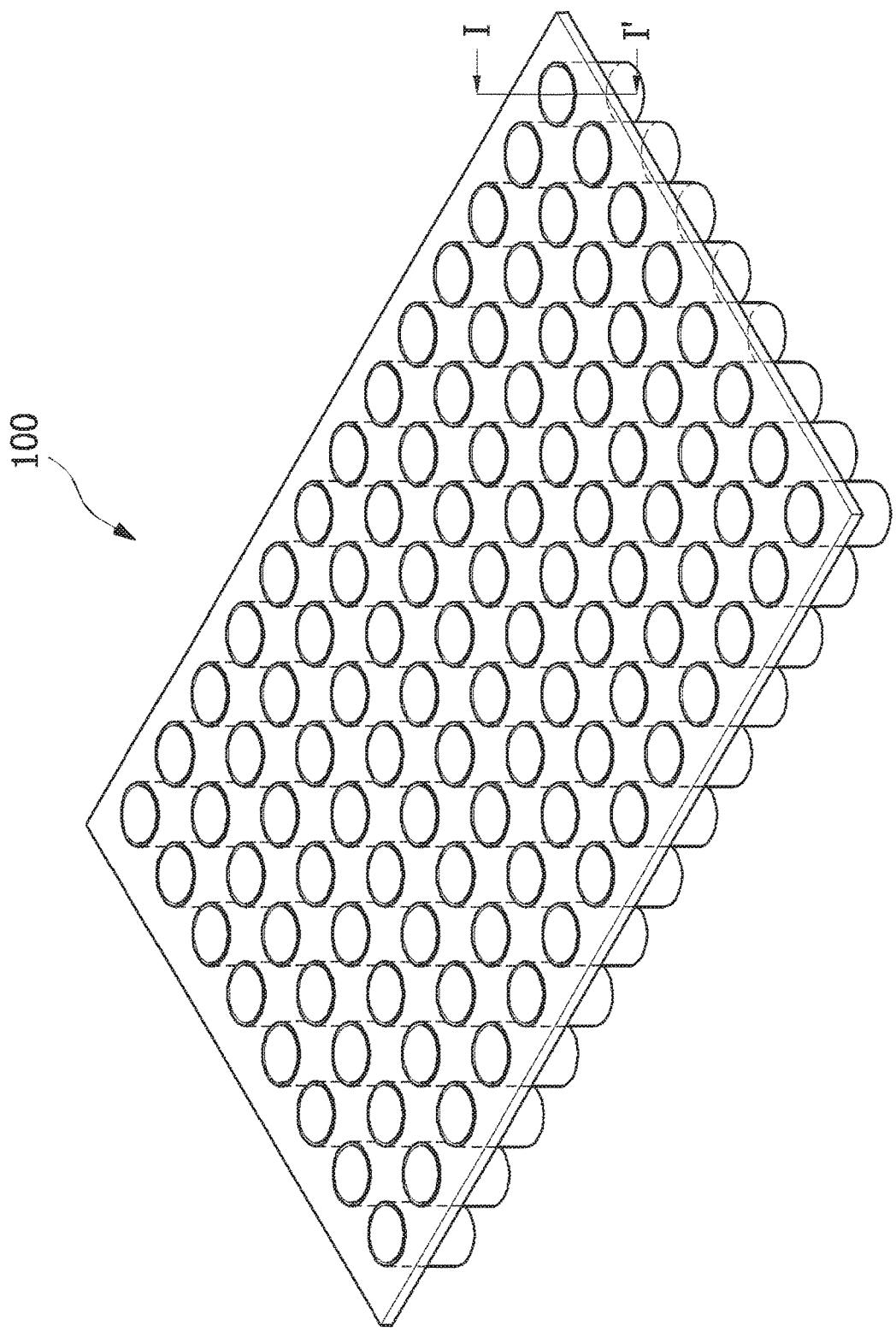
FIG. 1 is a perspective view illustrating a cell culture vessel according to an embodiment of the present invention.

Hereinafter, exemplary embodiments of the present invention will be described in detail with reference to the accompanying drawings so that those of ordinary skill in the art to which the present invention pertains may easily practice the present invention. The present invention may be implemented in various different forms and is not limited by the embodiments described herein. To clearly describe the present invention, parts unrelated to the description will be omitted, and like or similar elements will be denoted by like reference numerals throughout.

Figure 2:
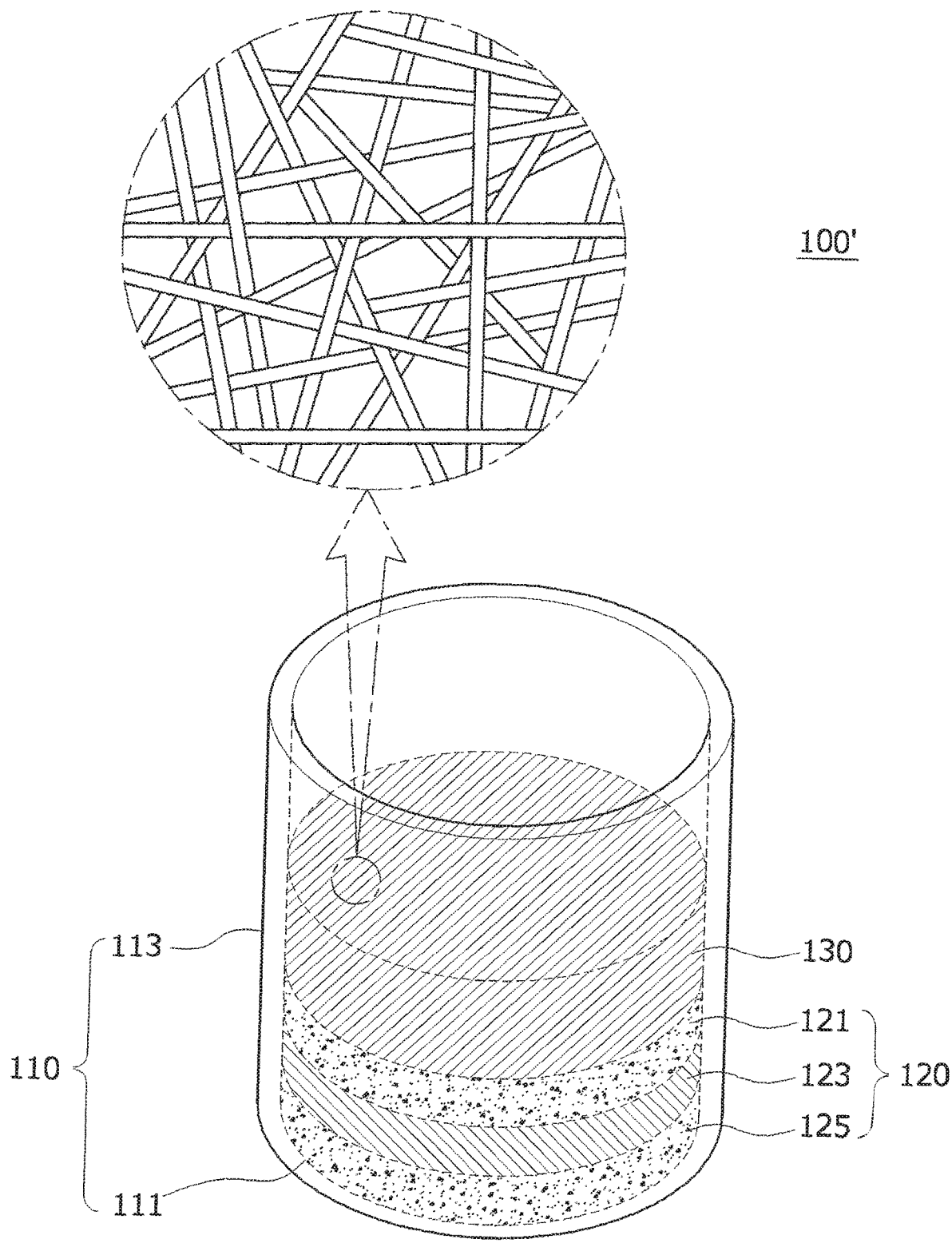
FIG. 2 is a perspective view illustrating one accommodating part among a plurality of accommodating parts constituting the cell culture vessel according to an embodiment of the present invention.

As illustrated in FIGS. 1 to 3, regarding a cell culture vessel 100 or 100' according to the present invention, the cell culture vessel 100, which includes accommodating parts 110 which are inner spaces each accommodating a cell culture support 130 therein, includes a fixing member 120 configured to fix the cell culture support 130 to a lower surface 111 of the accommodating part, wherein the fixing member 120 includes a first adhesive layer 125 attached to the lower surface 111 of the accommodating part, a second adhesive layer 121 attached to a lower surface of the cell culture support 130, and a support film 123 interposed between the first adhesive layer 125 and the second adhesive layer 121 and configured to perform a support function.

First, prior to describing each element of the cell culture vessel 100 or 100' according to the present invention, the reason why an adhesive force between the second adhesive layer 121 and the cell culture support 130 should be higher than an adhesive force between the first adhesive layer 125 and the lower surface 111 of the accommodating part will be described.

In the fixing member included in the cell culture vessel, when the adhesive force between the second adhesive layer 121 and the cell culture support 130 is low, shaking of the cell culture support may occur due to degradation of the adhesive force, uniform cell culture may thus be difficult, and, accordingly, cell culture and proliferation to a desired level may not be easy. When the adhesive force between the first adhesive layer 125 and the lower surface 111 of the accommodating part is high, cells may be damaged in the process of separating the fixing member 120 from the cell culture vessel 100.

Accordingly, in the fixing member included in the cell culture vessel according to the present invention, the adhesive force between the second adhesive layer 121 and the cell culture support 130 is implemented to be higher than the adhesive force between the first adhesive layer 125 and the lower surface 111 of the accommodating part. Preferably, an adhesive force ratio of the adhesive force between the first adhesive layer and the lower surface of the accommodating part to the adhesive force between the second adhesive layer and the cell culture support may be 1:1.3 to 1:4. More preferably, the adhesive force ratio of the adhesive force between the first adhesive layer and the lower surface of the accommodating part to the adhesive force between the second adhesive layer and the cell culture support may be 1:1.5 to 1:3.

When the adhesive force between the second adhesive layer and the cell culture support is lower than the adhesive force between the first adhesive layer and the lower surface of the accommodating part, the shaking of the cell culture support may occur due to degradation of the adhesive force, uniform cell culture may thus be difficult, and, accordingly, cell culture and proliferation to the desired level may not be easy.

Also, when the adhesive force ratio of the adhesive force between the first adhesive layer and the lower surface of the accommodating part to the adhesive force between the second adhesive layer and the cell culture support is less than 1:1.3, the shaking of the cell culture support may occur due to degradation of the adhesive force, uniform cell culture may thus be difficult, and, accordingly, cell culture and proliferation to the desired level may not be easy, and the cells may be damaged in the process of separating the fixing member 120 from the cell culture vessel 100. When the adhesive force ratio exceeds 1:4, the shaking of the cell culture support may occur due to degradation of an attaching force between the cell culture vessel 100 and the fixing member 120, uniform cell culture may thus be difficult, and, accordingly, cell culture and proliferation to the desired level may not be easy, and cells cultured in the cell culture support 130 may be damaged due to excessive mechanical stress acting thereon in the process of separating the cell culture support 130.

Hereinafter, each element of the cell culture vessel 100 according to the present invention will be described.

The accommodating parts 110 which are the inner spaces each accommodating the cell culture support 130 therein may have any shape as long as the shape is capable of accommodating the cell culture support. That is, the accommodating parts 110 are illustrated in the drawings as having a uniform cylindrical shape, but the present invention is not limited thereto. For example, each accommodating part 110 may have the shape of a beaker, a well plate, a bottle, a tube, or the like or may have a different shape and size in consideration of the size and type of cells being cultured.

Also, materials forming the cell culture vessel 100 are not particularly limited, and materials generally used in cell culture may be used. For example, resin materials such as polystyrene resin, polyester resin, polyethylene resin, polyethylene terephthalate resin, polypropylene resin, acrylonitrile butadiene styrene (ABS) resin, nylon, acrylic resin, fluorine resin, polycarbonate resin, polyurethane resin, methylpentene resin, phenol resin, melamine resin, epoxy resin, and vinyl chloride resin, resin materials including at least one or more of the above-listed resin materials whose surface is treated to be hydrophilic, and inorganic materials such as glass and quartz may be used.

Also, referring to FIGS. 2 and 3, the accommodating part 110 according to an embodiment of the present invention includes the lower surface 111 of the accommodating part and a side surface 113 of the accommodating part, which extends from the lower surface, and has a shape that is open upward. Although not illustrated in the drawings, an opening through which a culture solution may be introduced or discharged may be formed in the lower surface 111 of the accommodating part and the side surface 113 of the accommodating part. Also, a cover capable of covering the open upper portion may be further provided detachably and seal or open the accommodating part 110.

A diameter of the accommodating part 110 may be designed in consideration of the type and size of desired cells and whether the cells form colonies. A plurality of accommodating parts 110 each having a different diameter size may also be formed in one cell culture vessel 100.

The fixing member 120 and the cell culture support 130 each having the same shape and size as the lower surface 111 of the accommodating part 110 are fixed to the accommodating part 110. According to an embodiment of the present invention, the fixing member 120 and the cell culture support 130 may be formed to have a circular shape and accommodated in the accommodating part 110.

Meanwhile, cells capable of industrial cell culture may be largely classified into cell line cells obtained in succession from the primary culture cells and stem cells which are undifferentiated cells that may differentiate into various types of cells in embryos or adults. According to recent reports, stem cell culture requires much more sophisticated manipulations than cell line cell culture. That is, because stem cells are very sensitive to mechanical stress and other biochemical influences and thus even simple damage to the stem cells may cause apoptosis of the stem cells, it is not suitable for the stem cells to proliferate in a general cell culture medium that mechanically and chemically separates cultured cells.

Also, in the case of a known cell culture vessel, because a cell culture support is not fixed to the cell culture vessel in the process of culturing cells, cells may not proliferate to a desired level due to inhibition of uniform growth of the cells. Further, in the case of colony cells constituting a colony, even when cell colonies proliferated, not only the shape of the cell culture support in which the cells proliferated, but also the shapes of the cell colonies may be different according to physical and chemical methods of detaching from the cell culture support. When the shapes of the cell colonies are not uniform, each cultured cell colony may show a different reaction, and in this case, there is a problem in that, because it is not possible to derive reproducible results, the proliferated cell colonies are very unsuitable for use in testing and experimenting.

Therefore, in the present invention, the above-described relationship between the adhesive force between the second adhesive layer 121 and the cell culture support 130 and the adhesive force between the first adhesive layer 125 and the lower surface 111 of the accommodating part is satisfied so that cells which are very sensitive to damage, such as the above-described stem cells, may be easily separated from the cell culture vessel without causing damage to the cells. Also, by fixing the cell culture support 130, in which cells are cultured, to the cell culture vessel, environments which are physically, chemically, and mechanically the same may be provided to each cell to ensure that each cell proliferates uniformly to a desired level. In the case of colony cells constituting a colony, by separating colonies in a uniform shape and size without causing the cell-cell impact, improvement in utilization of cultured colonies can be expected.

More specifically, because the above-described relationship between the adhesive force between the second adhesive layer 121 and the cell culture support 130 and the adhesive force between the first adhesive layer 125 and the lower surface 111 of the accommodating part is satisfied and the support film 123 which performs the support function on the cell culture support 130 is included such that the cell culture support can be fixed without shaking, the same microenvironment can be provided to cells cultured in the cell culture support. That is, because non-uniform dispersion of a culture solution due to shaking of the support and tipping of the culture solution due to migration of the cells being cultured can be prevented in the process of culturing the cells, it is possible to contribute to uniform cell proliferation and cell proliferation to a desired level by applying the same mechanical, physical, and chemical stimulations to each cell.

Accordingly, the adhesive force between the first adhesive layer 125 and the lower surface 111 of the accommodating part may be in a range of 3 to 30 gf/inch, preferably, in a range of 5 to 25 gf/inch. When the adhesive force between the first adhesive layer 125 and the lower surface 111 of the accommodating part is less than 3 gf/inch, the shaking of the cell culture support may occur due to degradation of an attaching force between the cell culture vessel 100 and the fixing member 120, uniform cell culture may thus be problematic, and, accordingly, cell culture and proliferation to the desired level may not be easy. When the adhesive force exceeds 30 gf/inch, damage may be caused to the cells in the process of separating the fixing member 120 from the cell culture vessel 100.

Also, the adhesive force between the second adhesive layer 121 and the cell culture support 130 may be in a range of 7 to 60 gf/inch, preferably, in a range of 10 to 50 gf/inch. When the adhesive force between the second adhesive layer 121 and the cell culture support 130 is less than 7 gf/inch, the shaking of the cell culture support may occur due to degradation of the adhesive force, uniform cell culture may thus be difficult, and, accordingly, cell culture and proliferation to the desired level may not be easy. When the adhesive force exceeds 60 gf/inch, there is a concern that cells cultured in the cell culture support 130 may be damaged due to excessive mechanical stress acting thereon in the process of separating the cell culture support 130.

Meanwhile, it is self-evident that, even when the range of the adhesive force between the first adhesive layer 125 and the lower surface 111 of the accommodating part and the range of the adhesive force between the second adhesive layer 121 and the cell culture support 130 partially overlap, the present invention is implemented to satisfy the above-described relationship between the adhesive force between the first adhesive layer 125 and the lower surface 111 of the accommodating part and the adhesive force between the second adhesive layer 121 and the cell culture support 130.

The first adhesive layer 125 and the second adhesive layer 121 may be formed to include a component typically containing a substance harmless to cell culture. Preferably, the first adhesive layer 125 and the second adhesive layer 121 may include one or more selected from the group consisting of a silicone-based adhesive and a urethane-based adhesive, and more preferably, may include the silicone-based adhesive.

Also, the first adhesive layer 125 may have a thickness in a range of 7 to 55 µm, preferably, in a range of 10 to 50 µm. When the thickness of the first adhesive layer 125 is less than 7 µm, the first adhesive layer 125 may not be fixed to the lower surface 111 of the accommodating part, and thus the fixing member 120 may be detached by a washing solution (phosphate buffered saline (PBS), ethanol, media, and the like) in the process of cell culture. When the thickness exceeds 55 µm, there may be a problem in that detaching the fixing member 120 from the lower surface 111 of the accommodating part is not easy.

In addition, the second adhesive layer 121 may have a thickness in a range of 3 to 25 µm, preferably, in a range of 5 to 20 µm. When the thickness of the second adhesive layer 121 is less than 3 µm, a membrane may be detached during cell culture. When the thickness exceeds 25 µm, cultured cells may be damaged when detaching the cell culture support 130.

As a material of the support film 123 which is interposed between the first adhesive layer 125 and the second adhesive layer 121 and performs the support function, any material in the art that typically has a certain level of mechanical strength and is capable of performing the support function may be used without limitation. Preferably, the support film 123 may include one or more selected from the group consisting of polyethylene, polypropylene, polyimide, cross-linked polypropylene, nylon, polyurethane-based resin, acetate, polybenzimidazole, polyimideamide, polyetherimide, polyphenylene sulfide (PPS), polyethylene terephthalate (PET), polytrimethylene terephthalate (PTT), polybutylene terephthalate (PBT), polyvinylidene fluoride (PVDF), polytetrafluoroethylene (PTFE), polychlorotrifluoroethylene (PCTFE), and polyethylene tetrafluoroethylene (ETFE).

Also, the support film 123 may have a thickness in a range of 30 to 220 µm, preferably, in a range of 50 to 200 µm. When the thickness of the support film 123 is less than 30 µm, it may be difficult to obtain a sufficient mechanical strength. When the thickness exceeds 220 µm, it may not be easy to remove the support when recovering the cells.

Next, the cell culture support 130 included in the cell culture vessel 100 or 100' according to the present invention will be described.

The cell culture support 130 may be a fabric including any one or more of a knit, a woven fabric, and a nonwoven fabric.

For example, when the cell culture support 130 is formed of a knit, fibers included in the knit are oriented in longitudinal and transverse directions, the specific structure of the knit may include plain weave and twill weave, and a density of warp and weft is not particularly limited.

Also, for example, when the cell culture support 130 is formed of a woven fabric, the structure forming the woven fabric may be formed of a known knit structure. For example, the structure forming the woven fabric may include a weft knit and a wrap knit, but is not particularly limited thereto.

In addition, for example, when the cell culture support 130 is formed of a nonwoven fabric, the nonwoven fabric indicates that fibers are not oriented in the longitudinal and transverse directions, and known nonwoven fabrics such as a dry nonwoven fabric or a wet nonwoven fabric including a chemical bonding nonwoven fabric, a thermal bonding nonwoven fabric, and an airlay nonwoven fabric, a non-spandex nonwoven fabric, a needle-punching nonwoven fabric, and a meltblown may be used. For example, the nonwoven fabric may be a nanofiber web formed of electrospun nanofibers.

In this way, the fabric forming the cell culture support according to the present invention may be formed as various forms of fabrics in consideration of the size and type of cells, but the case in which the fabric is a nonwoven fabric is illustrated in FIG. 2.

Referring to an enlarged view of a part of the cell culture support 130 illustrated in FIG. 2, the fabric forming the cell culture support 130 of the present invention may be a yarn formed of a spun yarn, a filament yarn, a slitting yarn, or electrospun nanofibers.

When the yarn is a spun yarn or a filament yarn, the yarn may have a diameter in a range of 10 nm to 100 μm, preferably, in a range of 50 nm to 90 μm. However, the diameter is not limited thereto and may be changed to be suitable for the type and size of cells to be cultured and the shape and size of cell aggregates.

Also, the spun yarn may be manufactured using raw cotton by a known method. Also, the filament yarn may be manufactured by spinning by a known method, and the spinning may be a known spinning method such as chemical spinning or electrospinning.

Also, the slitting yarn may be manufactured by cutting a sheet-like fiber aggregate, fabric, or the like to have a predetermined width. Preferably, the slitting yarn may be a yarn manufactured by cutting a sheet-like fiber web having a three-dimensional network structure to have a predetermined width. In this case, the fiber web may be compressed at a constant pressure to improve the ease of a slitting process and increase the strength of the slitting yarn. For example, the slitting yarn may be a yarn obtained by cutting a fiber web whose basis weight is in a range of 0.1 to 100 g/m$^2$ to have a width in a range of 0.1 to 30 mm. When the fiber web is slit to a width less than 0.1 mm, there are problems in that the fiber web may not be easy to cut and the fiber web may easily break due to tension and rotary force applied during false twisting. Also, when the fiber web is slit to a width exceeding 30 mm, there is a problem in that the fiber web may be non-uniformly twisted during twisting.

Also, the electrospun nanofibers may be folded a plurality of times and arranged/stacked without any orientation to form a three-dimensional network structure. Alternatively, a plurality of nanofibers may be included, and each nanofiber may be independently folded and/or arranged/stacked without setting a fiber longitudinal direction to form a three-dimensional network structure. In this case, adhesion or fusion may occur between different surfaces in one strand of nanofiber and/or between surfaces of different nanofibers, and in this way, the three-dimensional network structure may become structurally more complicated, cells loaded on the support may migrate/proliferate into pores formed in the three-dimensional network structure, and it may be advantageous for culturing the cells as cell colonies having a three-dimensional shape/structure. Also, in order to increase the proliferation rate and survival rate of cells cultured inside/outside the support, it is important to supply nutrients necessary for cell proliferation. Because a flow path of a culture solution containing nutrients of nanofibers of the three-dimensional network structure is formed in a very complicated manner, the nutrients may be easily supplied to cells located inside the support, thereby preventing apoptosis and enhancing cell proliferation.

Next, the above-described yarn may be implemented by a known fiber forming component that can be manufactured in a fiber form. The yarn may be implemented by selecting a suitable material according to the type of yarn, and different materials may be selected according to special purposes such as requiring degradability. Accordingly, the present invention is not particularly limited thereto. The fiber forming component may include cellulose components such as cotton and hemp, protein components such as wool and silk, and natural fiber components such as mineral components. Alternatively, the fiber forming component may be a known artificial fiber component.

Meanwhile, the fiber forming component may include, according to purposes, any one or more non-biodegradable components selected from the group consisting of polystyrene (PS), polyethylene terephthalate (PET), polyethersulfone (PES), polyvinylidene fluoride (PVDF), polyacrylonitrile (PAN), polydimethylsiloxane (PDMS), polyamide, polyalkylene, poly(alkylene oxide), poly(amino acids), poly(allylamines), polyphosphazene, and polyethylene oxide-polypropylene oxide block copolymer and any one or more biodegradable components selected from the group consisting of polycaprolactone, polydioxanone, polyglycolic acid, poly(L-lactide) (PLLA), poly(DL-lactide-co-glycolide) (PLGA), polylactic acid, and polyvinyl alcohol.

Meanwhile, the above-described yarn may include a cell culturability enhancing substance in addition to the fiber forming component and may further include any one or more of an adhesive component and a bioactive component as the cell culturability enhancing substance. In this case, the adhesive component or the bioactive component may not be included inside the yarn, and the bioactive component may be fixed to a portion of an outer surface of the yarn by the adhesive component fixed to a region of the outer surface. Alternatively, the bioactive component may be provided to cover the entire adhesive component which is provided to cover the entire outer surface of the yarn.

Recently, research has been carried out on cell culture technology in a direction of realizing the actual in vivo intercellular environment in vitro. In order to form a cell culture environment that is similar to the in vivo cellular environment, various components included in the in vivo extracellular matrix (ECM) tend to be applied by being included in a culture solution during in vitro culture. However, when a substance capable of enhancing cell culture is included in the culture solution, there is a limitation in terms of continuously exposing the substance to the cells being cultured, and although the content of the substance should be increased in the culture solution for the continuous exposure, this increases the cost and is problematic in terms of proliferation efficiency.

Accordingly, the yarn is disposed at the support while the adhesive component and the bioactive component are fixed to a surface of the yarn according to an embodiment of the present invention, and thus cultured cells located on the yarn or in a space surrounded by the yarn are stimulated by the bioactive component. In this way, intracellular signal transduction is continued and amplified, and there is an advantage in that cell proliferation may be further accelerated.

The adhesive component may perform a function of fixing cells to be cultured on the cell support at an initial stage and preventing the cells loaded in the culture solution from floating and/or a function of fixing the bioactive component on the yarn and preventing desorption of the bioactive component from support fibers in the process in which the cells are cultured on the yarn. Any known adhesive component that is typically biocompatible and thus is not cytotoxic may be used without limitation as the adhesive component, but, preferably, the adhesive component may include one or more selected from the group consisting of proteins formed by repetition of amino acids of the sequence number 1 to sequence number 7 one to twenty times and protein in which at least two of the proteins are fused. In this way, there are advantages in that cytotoxicity is significantly decreased, the adhesive force of the bioactive component is excellent, and desorption of the bioactive component or isolation of the cells that occur as the adhesive component is dissolved in the culture solution during cell culture may be prevented.

Next, the bioactive component which may be included in the yarn will be described in more detail. The bioactive component may be a substance that directly/indirectly induces any one or more of adhesion, migration, growth, proliferation, and differentiation of cells so that cell culture is enhanced. The bioactive component may include, without limitation, any substance known to have such a function. For example, the bioactive component may include any one or more of cells and any one or more compounds selected from the group consisting of monoamine, amino acid, peptide, saccharide, lipid, protein, glucoprotein, glucolipid, proteoglycan, mucopolysaccharide, and nucleic acid. In this case, the monoamine includes a compound including primary amine such as catecholamine and indoleamine. Also, the peptide may include oligopeptide, and the protein may include polypeptide and be, for example, fibronectin. The saccharide may include monosaccharide, polysaccharide, oligosaccharide, and carbohydrate, and the lipid may be, for example, a steroid hormone.

Meanwhile, the bioactive component may include a motif. The motif may be natural peptide or recombinant peptide including a predetermined amino acid sequence included in any one or more selected from the group consisting of protein, glucoprotein, and proteoglycan included in a growth factor or an extracellular matrix. Specifically, the motif may include a predetermined amino acid sequence included in any one or more growth factors (GFs) selected from the group consisting of adrenomedullin, angiopoietin, bone morphogenetic protein (BMP), brain-derived neurotrophic factor (BDNF), epidermal growth factor (EGF), erythropoietin, fibroblast growth factor, glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), keratinocyte growth factor (KGF), migration-stimulating factor (MSF), myostatin (GDF-8), nerve growth factor (NGF), platelet-derived growth factor (PDGF), thrombopoietin (TPO), T-cell growth factor (TCGF), neuropilin, transforming growth factor-α (TGF-α), transforming growth factor-β (TGF-β), tumor necrosis factor-α (TNF-α), vascular endothelial growth factor (VEGF), IL-1, IL-2, IL-3, IL-4, IL-5, IL-6, and IL-7. Alternatively, the motif may include a predetermined amino acid sequence included in an extracellular matrix of any one or more selected from the group consisting of hyaluronic acid, heparin sulfate, chondroitin sulfate, dermatan sulfate, keratan sulfate, alginate, fibrin, fibrinogen, collagen, elastin, fibronectin, vitronectin, cadherin, and laminin. Also, the motif may include both the predetermined amino acid sequence included in the growth factor and the predetermined amino acid sequence included in the extracellular matrix. More preferably, the motif may include one or more selected from the group consisting of proteins formed to include amino acids of the sequence number 8 to sequence number 28 and protein in which at least two of the proteins are fused, but the motif is not limited thereto.

Meanwhile, the motif may also be covalently bonded to the above-described adhesive component and integrally formed therewith. For example, when the adhesive component is protein, the motif may be covalently bonded directly to N-terminus and/or C-terminus of polypeptide or may be covalently bonded by interposing heterologous peptides or polypeptides. In this case, the bioactive component may be more firmly attached to the yarn, and desorption of the bioactive component during cell culture may be minimized.

Also, when the bioactive component is a motif, the motif may be implemented to further include known mussel protein or a specific domain or motif of the mussel protein in order to enhance cell adhesion.

Meanwhile, the present invention may implement an implant for tissue engineering that includes cells cultured by transplanting cultured cells to a fabric which is the cell culture support included in the cell culture vessel according to an embodiment of the present invention. In this case, at outer surfaces of yarns and a portion including a space in which the yarns are spaced apart due to untwisting, the cells migrate to the space and are cultured. Accordingly, the cultured cells may be located inside the yarns. In this case, the yarns spaced apart from each other may be located between adjacent cells among the cultured cells. This may be more advantageous for cell culture because direct contact between the adjacent cells is prevented.

Also, the cells may include any one or more stem cells selected from the group consisting of totipotent stem cells, pluripotent stem cells, multipotent stem cells, oligopotent stem cells, and single stem cells and one or more of differentiated cells selected from the group consisting of hematopoietic stem cells, hepatocytes, fibrous cells, epithelial cells, mesothelial cells, endothelial cells, muscle cells, neurons, immunocytes, adipocytes, chondrocytes, osteocytes, blood cells, and skin cells. For example, the cells may be cells having an elongated shape in one direction rather than a spherical shape or may be cells having high mobility.

Also, when a material of the yarn is implemented using a fiber forming component that is harmless to the human body, the support to which the cultured cells are adhered may be directly transplanted into the human body, and in this way, there is an advantage in that the cultured cells may be more easily and stably engrafted into tissues.

Table 2 below is a table of the sequence listing showing the amino acid sequences according to the sequence numbers described in the present invention.

TABLE 2

| SEQ ID NO: | Amino acid sequence |
|---|---|
| 1 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser |

TABLE 2-continued

| SEQ ID NO: | Amino acid sequence |
|---|---|
| | Gly Gly Ser Tyr His Gly Ser Gly Tyr His Gly Tyr Lys Gly Lys Tyr Tyr Gly Lys Ala Lys Lys Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 2 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Gly Arg Gly Asp Ser Pro |
| 3 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Pro Trp Ala Asp Tyr Tyr Gly Pro Lys Tyr Gly Pro Pro Arg Arg Tyr Gly Gly Asn Tyr Asn Arg Tyr Gly Arg Arg Tyr Gly Gly Tyr Lys Gly Trp Asn Asn Gly Trp Lys Arg Gly Arg Trp Gly Arg Lys Tyr Tyr Gly Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Leu |
| 4 | Ala Asp Tyr Tyr Gly Pro Lys Tyr Gly Pro Pro Arg Arg Tyr Gly Gly Gly Asn Tyr Asn Arg Tyr Gly Arg Arg Tyr Gly Gly Tyr Lys Gly Trp Asn Asn Gly Trp Lys Arg Gly Arg Trp Gly Arg Lys Tyr Tyr |
| 5 | Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Gly Ser Ser |
| 6 | Ala Lys Pro Ser Tyr Pro Pro Thr Tyr Lys |
| 7 | Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 8 | Arg Gly Asp |
| 9 | Arg Gly Asp Ser |
| 10 | Arg Gly Asp Cys |
| 11 | Arg Gly Asp Val |
| 12 | Arg Gly Asp Ser Pro Ala Ser Ser Lys Pro |
| 13 | Gly Arg Gly Asp Ser |
| 14 | Gly Arg Gly Asp Thr Pro |
| 15 | Gly Arg Gly Asp Ser Pro |
| 16 | Gly Arg Gly Asp Ser Pro Cys |
| 17 | Tyr Arg Gly Asp Ser |
| 18 | Ser Pro Pro Arg Arg Ala Arg Val Thr |
| 19 | Trp Gln Pro Pro Arg Ala Arg Ile |
| 20 | Asn Arg Trp His Ser Ile Tyr Ile Thr Arg Phe Gly |

TABLE 2-continued

| SEQ ID NO: | Amino acid sequence |
|---|---|
| 21 | Arg Lys Arg Leu Gln Val Gln Leu Ser Ile Arg Thr |
| 22 | Lys Ala Phe Asp Ile Thr Tyr Val Arg Leu Lys Phe |
| 23 | Ile Lys Val Ala Asn |
| 24 | Lys Lys Gln Arg Phe Arg His Arg Asn Arg Lys Gly Tyr Arg Ser Gln |
| 25 | Val Ala Glu Ile Asp Gly Ile Gly Leu |
| 26 | Pro His Ser Arg Asn Arg Gly Asp Ser Pro |
| 27 | Asn Arg Trp His Ser Ile Tyr Ile Thr Arg Phe Gly |
| 28 | Thr Trp Tyr Lys Ile Ala Phe Gln Arg Asn Arg Lys |

MODES OF THE INVENTION

The present invention will be described in more detail using the following examples, but the examples are not intended to limit the scope of the present invention and should be interpreted as assisting in understanding of the present invention.

Example 1

First, a fixing member was manufactured by forming a first adhesive layer having a thickness of 30 μm on a lower surface of a polyester film (polyester, Segi Convertech Co., Ltd.) having a thickness of 75 μm, which was a support film, by using a silicone-based adhesive and forming a second adhesive layer having a thickness of 15 μm on an upper surface of the polyester film by using a silicone-based adhesive.

Then, a first spinning solution, which included 0.3 mg/ml of fibronectin (RGD-based) as an adhesive substance, 0.3 mg/ml of laminin as a bioactive substance, 13 wt % of PLGA as a fiber forming component, and a total of 87 wt % of tetrahydrofurane (THF) and dimethylformamide (DMF) in a weight ratio of 3:7 as a solvent, was electrospun using an electrospinning device in an environment having a temperature of 30° C. and relative humidity (RH) of 60% under conditions in which an applied voltage was 25 kV, a distance from a current collector and a spinning nozzle was 25 cm, and a discharge rate was 0.05 ml/hole. In this way, a nanofiber web formed of nanofibers having an average diameter of 600 nm was obtained. By a method of performing calendering two times at a temperature of 130° C. and a pressure of 4 kPa on the obtained nanofiber web, a cell culture support, which was a fabric whose basis weight was 15.1 g/m², thickness was 25 μm, an average pore size was 0.8 μm, and air permeability was 5 cfm, was manufactured and was attached to come in contact with the second adhesive layer of the manufactured fixing member.

Then, a cell culture vessel was manufactured by attaching the fixing member, to which the cell culture support was attached, to a lower surface of an accommodating part of a vessel for cell culture, which was formed of polyethylene terephthalate resin and included the accommodating part, such that the first adhesive layer was in contact with the lower surface of the accommodating part.

In this case, an adhesive force between the first adhesive layer and the lower surface of the accommodating part was 25 gf/inch, and an adhesive force between the second adhesive layer and the cell culture support was 50 gf/inch.

Examples 2 to 11 and Comparative Example 1

A cell culture vessel was manufactured identically as in Example 1 except for changing the adhesive force between the first adhesive layer and the lower surface of the accommodating part, the adhesive force between the second adhesive layer and the cell culture support, the thickness of the first adhesive layer, the thickness of the second adhesive layer, and the thickness of the support film as shown in Table 3 and Table 4 below.

Experimental Example

Fibroblasts (HS27) were loaded in each cell culture vessel manufactured in the examples and the comparative example and then were made to proliferate for 4 days in a 10% complete medium. In this case, the 10% complete medium was manufactured by mixing Ham's F12 medium to Dulbecco's modified eagle medium (DMEM) in a volume ratio of 1:1.5 and then adding 7 vol % of fetal bovine serum, 65 U/ml of penicillin, and 65 μg/ml of streptomycin in the mixture. Then, physical properties were evaluated as follows and shown in Table 3 and Table 4.

1. Evaluation of Cell Culture Uniformity

A laminate of the cell culture support and the fixing member was separated from each cell culture vessel which included the proliferated fibroblasts, the cell culture support was separated from the laminate, a cell count was measured using a cell counter, and then, based on the cell count measured in Example 1 as 100%, the cell counts of other examples and the comparative example were relatively shown.

In this case, a small cell count indicates that cell culture and proliferation are degraded because of a difficulty in uniform cell culture that is caused by non-uniform dispersion of a culture solution due to shaking of the support and tipping of the culture solution due to migration of the cells being cultured.

2. Evaluation of Cell Damage

A laminate of the cell culture support and the fixing member was separated from each cell culture vessel which included the proliferated fibroblasts, the cell culture support was separated from the laminate, a cell count was measured using a cell counter, and, through a cell viability assay, a ratio of viable cells to the total cells was measured to evaluate cell damage.

TABLE 3

| | Type | Example 1 | Example 2 | Example 3 | Example 4 | Example 5 | Example 6 |
|---|---|---|---|---|---|---|---|
| First adhesive layer | Adhesive force against lower surface of accommodating part (gf/inch), a | 25 | 5 | 35 | 25 | 15 | 15 |
| | Thickness(μm) | 30 | 30 | 30 | 30 | 30 | 30 |
| Second adhesive layer | Adhesive force against cell culture support (gf/inch), b | 50 | 10 | 38.5 | 37.5 | 45 | 75 |
| | Thickness(μm) | 15 | 15 | 15 | 15 | 15 | 15 |
| Adhesive force ratio of a to b | | 1:2 | 1:2 | 1:1.1 | 1:1.5 | 1:3 | 1:5 |
| Support film | Thickness(μm) | 75 | 75 | 75 | 75 | 75 | 75 |
| Evaluation of cell culture uniformity (%) | | 100 | 95.4 | 99.2 | 99.8 | 97.2 | 97.0 |
| Evaluation of cell damage (%) | | 95.1 | 93.0 | 78.5 | 94.7 | 94.8 | 76.6 |

TABLE 4

| | Type | Example 7 | Example 8 | Example 9 | Example 10 | Example 11 | Comparative Example 1 |
|---|---|---|---|---|---|---|---|
| First adhesive layer | Adhesive force against lower surface of accommodating part (gf/inch), a | 1 | 25 | 25 | 25 | 25 | 10 |
| | Thickness(μm) | 30 | 5 | 60 | 30 | 30 | 30 |
| Second adhesive layer | Adhesive force against cell culture support (gf/inch), b | 2 | 50 | 50 | 50 | 50 | 5 |
| | Thickness(μm) | 15 | 15 | 15 | 1 | 30 | 15 |
| Adhesive force ratio of a to b | | 1:2 | 1:2 | 1:2 | 1:1.1 | 1:1.5 | 1:0.5 |
| Support film | Thickness(μm) | 75 | 75 | 75 | 75 | 75 | 75 |
| Evaluation of cell culture uniformity (%) | | 40.3 | 82.7 | 96.3 | 83.5 | 93.2 | 62.7 |
| Evaluation of cell damage (%) | | 67.9 | 92.8 | 81.1 | 89.6 | 80.4 | 84.5 |

From Table 3 and Table 4 above, it can be confirmed that, in Examples 1, 2, 4, and 5 in which all of the adhesive force between the first adhesive layer and the lower surface of the accommodating part, the adhesive force between the second adhesive layer and the cell support culture, the thickness of the first adhesive layer, the thickness of the second adhesive layer, and the thickness of the support film were satisfied, cell culture uniformity was better and cell damage did not occur as compared with Examples 3, 6 to 11, and Comparative Example 1 in which at least one or more of the above was not satisfied.

Exemplary embodiments of the present invention have been described above, but the idea of the present invention is not limited by the embodiments presented herein. Those of ordinary skill in the art who understand the idea of the present invention may easily propose other embodiments by adding, changing, or omitting elements within the equivalent scope, such embodiments also fall within the scope of the present invention.

The invention claimed is:

1. A cell culture vessel including an accommodating part which is an inner space accommodating a cell culture support therein, the cell culture vessel comprising:
 a fixing member configured to fix the cell culture support which is a nanofiber web formed of nanofiber to a lower surface of the accommodating part,
 wherein the fixing member includes a first adhesive layer attached to the lower surface of the accommodating part, a second adhesive layer attached to a lower surface of the cell culture support, and a support film interposed between the first adhesive layer and the second adhesive layer and configured to perform a support function, and
 an adhesive force between the second adhesive layer and the cell culture support is higher than an adhesive force between the first adhesive layer and the lower surface of the accommodating part,
 wherein the first adhesive layer has a thickness in a range of 7 to 55 μm,
 wherein the second adhesive layer has a thickness in a range of 3 to 25 μm,
 wherein the adhesive force between the second adhesive layer and the cell culture support is in a range of 7 to 60 gf/inch, and
 wherein an adhesive force ratio of the adhesive force between the first adhesive layer and the lower surface of the accommodating part to the adhesive force between the second adhesive layer and the cell culture support is 1:1.5 to 1:3.

2. The cell culture vessel of claim 1, wherein the adhesive force between the first adhesive layer and the lower surface of the accommodating part is in a range of 3 to 30 gf/inch.

3. The cell culture vessel of claim 1, wherein the first adhesive layer and the second adhesive layer each independently include one or more selected from the group consisting of a silicone-based adhesive and a urethane-based adhesive.

4. The cell culture vessel of claim 1, wherein the support film has a thickness in a range of 30 to 220 μm.

5. The cell culture vessel of claim 1, wherein the support film includes one or more selected from the group consisting of polyethylene, polypropylene, polyimide, cross-linked polypropylene, nylon, polyurethane-based resin, acetate, polybenzimidazole, polyimideamide, polyetherimide, polyphenylene sulfide (PPS), polyethylene terephthalate (PET), polytrimethylene terephthalate (PTT), polybutylene terephthalate (PBT), polyvinylidene fluoride (PVDF), polytetrafluoroethylene (PTFE), polychlorotrifluoroethylene (PCTFE), and polyethylene tetrafluoroethylene (ETFE).

6. The cell culture vessel of claim 1, wherein the nanofiber web includes a cell culture enhancing substance.

7. The cell culture vessel of claim 6, wherein the cell culture enhancing substance includes a bioactive component that induces any one or more of adhesion, migration, growth, proliferation, and differentiation of cells.

* * * * *

SEQUENCE LISTING

<160> NUMBER OF SEQ ID NOS: 28

<210> SEQ ID NO 1
<211> LENGTH: 196
<212> TYPE: PRT
<213> ORGANISM: Artificial
<220> FEATURE:
<223> OTHER INFORMATION: Motif for cell culture scaffold

<400> SEQUENCE: 1

Met Ala Lys Pro Ser Tyr Pro Pro Thr Tyr Lys Ala Lys Pro Ser Tyr
1               5                   10                  15

```
Pro Pro Thr Tyr Lys Ala Lys Pro Ser Tyr Pro Pro Thr Tyr Lys Ala
            20                  25                  30
Lys Pro Ser Tyr Pro Pro Thr Tyr Lys Ala Lys Pro Ser Tyr Pro Pro
            35                  40                  45
Thr Tyr Lys Ala Lys Pro Ser Tyr Pro Pro Thr Tyr Lys Ser Ser Glu
         50                  55                  60
Glu Tyr Lys Gly Gly Tyr Tyr Pro Gly Asn Thr Tyr His Tyr His Ser
 65                  70                  75                  80
Gly Gly Ser Tyr His Gly Ser Gly Tyr His Gly Gly Tyr Lys Gly Lys
                 85                  90                  95
Tyr Tyr Gly Lys Ala Lys Lys Tyr Tyr Tyr Lys Tyr Lys Asn Ser Gly
            100                 105                 110
Lys Tyr Lys Tyr Leu Lys Lys Ala Arg Lys Tyr His Arg Lys Gly Tyr
            115                 120                 125
Lys Lys Tyr Tyr Gly Gly Ser Ser Ala Lys Pro Ser Tyr Pro Pro Thr
            130                 135                 140
Tyr Lys Ala Lys Pro Ser Tyr Pro Pro Thr Tyr Lys Ala Lys Pro Ser
145                 150                 155                 160
Tyr Pro Pro Thr Tyr Lys Ala Lys Pro Ser Tyr Pro Pro Thr Tyr Lys
                165                 170                 175
Ala Lys Pro Ser Tyr Pro Pro Thr Tyr Lys Ala Lys Pro Ser Tyr Pro
            180                 185                 190
Pro Thr Tyr Lys
            195

<210> SEQ ID NO 2
<211> LENGTH: 202
<212> TYPE: PRT
<213> ORGANISM: Artificial
<220> FEATURE:
<223> OTHER INFORMATION: Motif for cell culture scaffold

<400> SEQUENCE: 2

Met Ala Lys Pro Ser Tyr Pro Pro Thr Tyr Lys Ala Lys Pro Ser Tyr
  1               5                  10                  15
Pro Pro Thr Tyr Lys Ala Lys Pro Ser Tyr Pro Pro Thr Tyr Lys Ala
            20                  25                  30
Lys Pro Ser Tyr Pro Pro Thr Tyr Lys Ala Lys Pro Ser Tyr Pro Pro
            35                  40                  45
Thr Tyr Lys Ala Lys Pro Ser Tyr Pro Pro Thr Tyr Lys Ser Ser Glu
         50                  55                  60
Glu Tyr Lys Gly Gly Tyr Tyr Pro Gly Asn Thr Tyr His Tyr His Ser
 65                  70                  75                  80
Gly Gly Ser Tyr His Gly Ser Gly Tyr His Gly Gly Tyr Lys Gly Lys
                 85                  90                  95
Tyr Tyr Gly Lys Ala Lys Lys Tyr Tyr Tyr Lys Tyr Lys Asn Ser Gly
            100                 105                 110
Lys Tyr Lys Tyr Leu Lys Lys Ala Arg Lys Tyr His Arg Lys Gly Tyr
            115                 120                 125
Lys Lys Tyr Tyr Gly Gly Ser Ser Ala Lys Pro Ser Tyr Pro Pro Thr
            130                 135                 140
Tyr Lys Ala Lys Pro Ser Tyr Pro Pro Thr Tyr Lys Ala Lys Pro Ser
145                 150                 155                 160
Tyr Pro Pro Thr Tyr Lys Ala Lys Pro Ser Tyr Pro Pro Thr Tyr Lys
                165                 170                 175
```

```
Ala Lys Pro Ser Tyr Pro Pro Thr Tyr Lys Ala Lys Pro Ser Tyr Pro
                180                 185                 190

Pro Thr Tyr Lys Gly Arg Gly Asp Ser Pro
        195                 200

<210> SEQ ID NO 3
<211> LENGTH: 172
<212> TYPE: PRT
<213> ORGANISM: Artificial
<220> FEATURE:
<223> OTHER INFORMATION: Motif for cell culture scaffold

<400> SEQUENCE: 3

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
                20                  25                  30

Lys Pro Ser Tyr Pro Pro Thr Tyr Lys Ala Lys Pro Ser Tyr Pro Pro
                35                  40                  45

Thr Tyr Lys Ala Lys Pro Ser Tyr Pro Pro Thr Tyr Lys Pro Trp Ala
        50                  55                  60

Asp Tyr Tyr Gly Pro Lys Tyr Gly Pro Pro Arg Arg Tyr Gly Gly Gly
65                  70                  75                  80

Asn Tyr Asn Arg Tyr Gly Arg Arg Tyr Gly Gly Tyr Lys Gly Trp Asn
                85                  90                  95

Asn Gly Trp Lys Arg Gly Arg Trp Gly Arg Lys Tyr Tyr Gly Ser Ala
                100                 105                 110

Lys Pro Ser Tyr Pro Pro Thr Tyr Lys Ala Lys Pro Ser Tyr Pro Pro
                115                 120                 125

Thr Tyr Lys Ala Lys Pro Ser Tyr Pro Pro Thr Tyr Lys Ala Lys Pro
        130                 135                 140

Ser Tyr Pro Pro Thr Tyr Lys Ala Lys Pro Ser Tyr Pro Pro Thr Tyr
145                 150                 155                 160

Lys Ala Lys Pro Ser Tyr Pro Pro Thr Tyr Lys Leu
                165                 170

<210> SEQ ID NO 4
<211> LENGTH: 46
<212> TYPE: PRT
<213> ORGANISM: Artificial
<220> FEATURE:
<223> OTHER INFORMATION: Motif for cell culture scaffold

<400> SEQUENCE: 4

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
                20                  25                  30

Asn Asn Gly Trp Lys Arg Gly Arg Trp Gly Arg Lys Tyr Tyr
            35                  40                  45

<210> SEQ ID NO 5
<211> LENGTH: 76
<212> TYPE: PRT
<213> ORGANISM: Artificial
<220> FEATURE:
<223> OTHER INFORMATION: Motif for cell culture scaffold

<400> SEQUENCE: 5

Ser Ser Glu Glu Tyr Lys Gly Gly Tyr Tyr Pro Gly Asn Thr Tyr His
```

```
              1               5                  10                 15
Tyr His Ser Gly Gly Ser Tyr His Gly Ser Gly Tyr His Gly Gly Tyr
              20                 25                 30
Lys Gly Lys Tyr Tyr Gly Lys Ala Lys Lys Tyr Tyr Lys Tyr Lys
        35                 40                 45
Asn Ser Gly Lys Tyr Lys Tyr Leu Lys Lys Ala Arg Lys Tyr His Arg
        50                 55                 60
Lys Gly Tyr Lys Lys Tyr Tyr Gly Gly Ser Ser
65                 70                 75

<210> SEQ ID NO 6
<211> LENGTH: 10
<212> TYPE: PRT
<213> ORGANISM: Artificial
<220> FEATURE:
<223> OTHER INFORMATION: Motif for cell culture scaffold

<400> SEQUENCE: 6

Ala Lys Pro Ser Tyr Pro Pro Thr Tyr Lys
1               5                  10

<210> SEQ ID NO 7
<211> LENGTH: 60
<212> TYPE: PRT
<213> ORGANISM: Artificial
<220> FEATURE:
<223> OTHER INFORMATION: Motif for cell culture scaffold

<400> SEQUENCE: 7

Ala Lys Pro Ser Tyr Pro Pro Thr Tyr Lys Ala Lys Pro Ser Tyr Pro
1               5                  10                 15
Pro Thr Tyr Lys Ala Lys Pro Ser Tyr Pro Pro Thr Tyr Lys Ala Lys
              20                 25                 30
Pro Ser Tyr Pro Pro Thr Tyr Lys Ala Lys Pro Ser Tyr Pro Pro Thr
        35                 40                 45
Tyr Lys Ala Lys Pro Ser Tyr Pro Pro Thr Tyr Lys
        50                 55                 60

<210> SEQ ID NO 8
<211> LENGTH: 3
<212> TYPE: PRT
<213> ORGANISM: Artificial
<220> FEATURE:
<223> OTHER INFORMATION: Motif for cell culture scaffold

<400> SEQUENCE: 8

Arg Gly Asp
1

<210> SEQ ID NO 9
<211> LENGTH: 4
<212> TYPE: PRT
<213> ORGANISM: Artificial
<220> FEATURE:
<223> OTHER INFORMATION: Motif for cell culture scaffold

<400> SEQUENCE: 9

Arg Gly Asp Ser
1

<210> SEQ ID NO 10
<211> LENGTH: 4
<212> TYPE: PRT
```

```
<213> ORGANISM: Artificial
<220> FEATURE:
<223> OTHER INFORMATION: Motif for cell culture scaffold

<400> SEQUENCE: 10

Arg Gly Asp Cys
1

<210> SEQ ID NO 11
<211> LENGTH: 4
<212> TYPE: PRT
<213> ORGANISM: Artificial
<220> FEATURE:
<223> OTHER INFORMATION: Motif for cell culture scaffold

<400> SEQUENCE: 11

Arg Gly Asp Val
1

<210> SEQ ID NO 12
<211> LENGTH: 10
<212> TYPE: PRT
<213> ORGANISM: Artificial
<220> FEATURE:
<223> OTHER INFORMATION: Motif for cell culture scaffold

<400> SEQUENCE: 12

Arg Gly Asp Ser Pro Ala Ser Ser Lys Pro
1               5                   10

<210> SEQ ID NO 13
<211> LENGTH: 5
<212> TYPE: PRT
<213> ORGANISM: Artificial
<220> FEATURE:
<223> OTHER INFORMATION: Motif for cell culture scaffold

<400> SEQUENCE: 13

Gly Arg Gly Asp Ser
1               5

<210> SEQ ID NO 14
<211> LENGTH: 6
<212> TYPE: PRT
<213> ORGANISM: Artificial
<220> FEATURE:
<223> OTHER INFORMATION: Motif for cell culture scaffold

<400> SEQUENCE: 14

Gly Arg Gly Asp Thr Pro
1               5

<210> SEQ ID NO 15
<211> LENGTH: 6
<212> TYPE: PRT
<213> ORGANISM: Artificial
<220> FEATURE:
<223> OTHER INFORMATION: Motif for cell culture scaffold

<400> SEQUENCE: 15

Gly Arg Gly Asp Ser Pro
1               5

<210> SEQ ID NO 16
<211> LENGTH: 7
<212> TYPE: PRT
<213> ORGANISM: Artificial
```

<220> FEATURE:
<223> OTHER INFORMATION: Motif for cell culture scaffold

<400> SEQUENCE: 16

Gly Arg Gly Asp Ser Pro Cys
1               5

<210> SEQ ID NO 17
<211> LENGTH: 5
<212> TYPE: PRT
<213> ORGANISM: Artificial
<220> FEATURE:
<223> OTHER INFORMATION: Motif for cell culture scaffold

<400> SEQUENCE: 17

Tyr Arg Gly Asp Ser
1               5

<210> SEQ ID NO 18
<211> LENGTH: 9
<212> TYPE: PRT
<213> ORGANISM: Artificial
<220> FEATURE:
<223> OTHER INFORMATION: Motif for cell culture scaffold

<400> SEQUENCE: 18

Ser Pro Pro Arg Arg Ala Arg Val Thr
1               5

<210> SEQ ID NO 19
<211> LENGTH: 8
<212> TYPE: PRT
<213> ORGANISM: Artificial
<220> FEATURE:
<223> OTHER INFORMATION: Motif for cell culture scaffold

<400> SEQUENCE: 19

Trp Gln Pro Pro Arg Ala Arg Ile
1               5

<210> SEQ ID NO 20
<211> LENGTH: 12
<212> TYPE: PRT
<213> ORGANISM: Artificial
<220> FEATURE:
<223> OTHER INFORMATION: Motif for cell culture scaffold

<400> SEQUENCE: 20

Asn Arg Trp His Ser Ile Tyr Ile Thr Arg Phe Gly
1               5                   10

<210> SEQ ID NO 21
<211> LENGTH: 12
<212> TYPE: PRT
<213> ORGANISM: Artificial
<220> FEATURE:
<223> OTHER INFORMATION: Motif for cell culture scaffold

<400> SEQUENCE: 21

Arg Lys Arg Leu Gln Val Gln Leu Ser Ile Arg Thr
1               5                   10

<210> SEQ ID NO 22
<211> LENGTH: 12
<212> TYPE: PRT
<213> ORGANISM: Artificial
<220> FEATURE:

```
<223> OTHER INFORMATION: Motif for cell culture scaffold

<400> SEQUENCE: 22

Lys Ala Phe Asp Ile Thr Tyr Val Arg Leu Lys Phe
1               5                   10

<210> SEQ ID NO 23
<211> LENGTH: 5
<212> TYPE: PRT
<213> ORGANISM: Artificial
<220> FEATURE:
<223> OTHER INFORMATION: Motif for cell culture scaffold

<400> SEQUENCE: 23

Ile Lys Val Ala Asn
1               5

<210> SEQ ID NO 24
<211> LENGTH: 16
<212> TYPE: PRT
<213> ORGANISM: Artificial
<220> FEATURE:
<223> OTHER INFORMATION: Motif for cell culture scaffold

<400> SEQUENCE: 24

Lys Lys Gln Arg Phe Arg His Arg Asn Arg Lys Gly Tyr Arg Ser Gln
1               5                   10                  15

<210> SEQ ID NO 25
<211> LENGTH: 9
<212> TYPE: PRT
<213> ORGANISM: Artificial
<220> FEATURE:
<223> OTHER INFORMATION: Motif for cell culture scaffold

<400> SEQUENCE: 25

Val Ala Glu Ile Asp Gly Ile Gly Leu
1               5

<210> SEQ ID NO 26
<211> LENGTH: 10
<212> TYPE: PRT
<213> ORGANISM: Artificial
<220> FEATURE:
<223> OTHER INFORMATION: Motif for cell culture scaffold

<400> SEQUENCE: 26

Pro His Ser Arg Asn Arg Gly Asp Ser Pro
1               5                   10

<210> SEQ ID NO 27
<211> LENGTH: 12
<212> TYPE: PRT
<213> ORGANISM: Artificial
<220> FEATURE:
<223> OTHER INFORMATION: Motif for cell culture scaffold

<400> SEQUENCE: 27

Asn Arg Trp His Ser Ile Tyr Ile Thr Arg Phe Gly
1               5                   10

<210> SEQ ID NO 28
<211> LENGTH: 12
<212> TYPE: PRT
<213> ORGANISM: Artificial
<220> FEATURE:
<223> OTHER INFORMATION: Motif for cell culture scaffold
```

```
<400> SEQUENCE: 28

Thr Trp Tyr Lys Ile Ala Phe Gln Arg Asn Arg Lys
1               5                   10
```